(12) United States Patent
McCrary et al.

(10) Patent No.: US 8,834,450 B1
(45) Date of Patent: Sep. 16, 2014

(54) ANTIMICROBIAL FLUID SUCTIONING DEVICE

(75) Inventors: Craig R. McCrary, Valencia, CA (US); Thomas R. Thornbury, Los Aneles, CA (US); Arnold M. Heyman, Los Angeles, CA (US)

(73) Assignee: Neotech Products, Inc., Valencia, CA (US)

( * ) Notice: Subject to any disclaimer, the term of this patent is extended or adjusted under 35 U.S.C. 154(b) by 20 days.

(21) Appl. No.: 13/200,887

(22) Filed: Oct. 3, 2011

Related U.S. Application Data

(63) Continuation-in-part of application No. 12/217,593, filed on Jul. 8, 2008, now Pat. No. 8,029,497.

(51) Int. Cl.
*A61M 1/00* (2006.01)

(52) U.S. Cl.
USPC .......................................................... 604/540

(58) Field of Classification Search
CPC .. A61M 1/008; A61M 1/0084; A61M 1/0088
USPC .......................................................... 604/540
See application file for complete search history.

(56) References Cited

U.S. PATENT DOCUMENTS

| | | | | |
|---|---|---|---|---|
| 2,468,338 A | * | 4/1949 | Macwilliam | ............... 285/251 |
| 2,816,781 A | * | 12/1957 | Woodling | ................ 285/222.4 |
| 3,032,358 A | * | 5/1962 | Rolston | .......................... 285/247 |
| 3,319,628 A | | 5/1967 | Halligan | |
| D223,247 S | * | 4/1972 | Brodsky | ....................... D24/112 |
| 4,266,814 A | | 5/1981 | Gallagher | |
| 4,496,268 A | * | 1/1985 | Ressi di Cervia | ............. 405/133 |
| 4,729,765 A | | 3/1988 | Eckels et al. | |
| 5,496,268 A | | 3/1996 | Peria | |
| 5,507,535 A | | 4/1996 | McKamey et al. | |
| 5,624,139 A | * | 4/1997 | Van Kooten | ..................... 285/31 |
| D435,101 S | * | 12/2000 | Graneto, III | ................. D24/108 |
| 6,158,784 A | * | 12/2000 | Lavender | ....................... 285/239 |
| D449,378 S | | 10/2001 | Rogone et al. | |
| 6,958,050 B1 | | 10/2005 | Choski et al. | |
| 7,131,839 B2 | * | 11/2006 | March | ............................. 433/95 |
| 7,229,429 B2 | * | 6/2007 | Martin et al. | ................... 604/43 |
| 7,306,577 B2 | * | 12/2007 | Lemoine et al. | ............. 604/118 |
| D590,056 S | * | 4/2009 | McCrary et al. | ............. D24/108 |
| 7,635,361 B2 | * | 12/2009 | McCrary et al. | ............. 604/541 |
| 7,766,396 B1 | * | 8/2010 | Elbaz | ............................ 285/397 |
| 8,029,497 B2 | * | 10/2011 | McCrary et al. | ............. 604/540 |
| 2005/0175961 A1 | * | 8/2005 | March | ............................. 433/91 |
| 2008/0145816 A1 | * | 6/2008 | Hershey et al. | ................. 433/95 |

* cited by examiner

*Primary Examiner* — Susan Su
*Assistant Examiner* — Guy K Townsend
(74) *Attorney, Agent, or Firm* — William W. Haefliger

(57) ABSTRACT

A mucous suction device, comprising in combination, a longitudinally elongated, generally tubular, one-piece plastic body, the body having an axially elongated tapered, first portion extending toward an inlet proximate one end of the body, the body having an axially elongated second portion extending toward an outlet proximate an opposite end of the body, radially outwardly extending annular retention rings on said body second portion, the rings having sharp annular peripheries and the rings being axially resiliently flexible and axially spaced apart, and there being body side porting between the body first and second portions, the side porting being manually controllable to control suction exertion, there being antimicrobial substance associated with body outwardly presented plastic surface extent at the first and second portions.

17 Claims, 3 Drawing Sheets

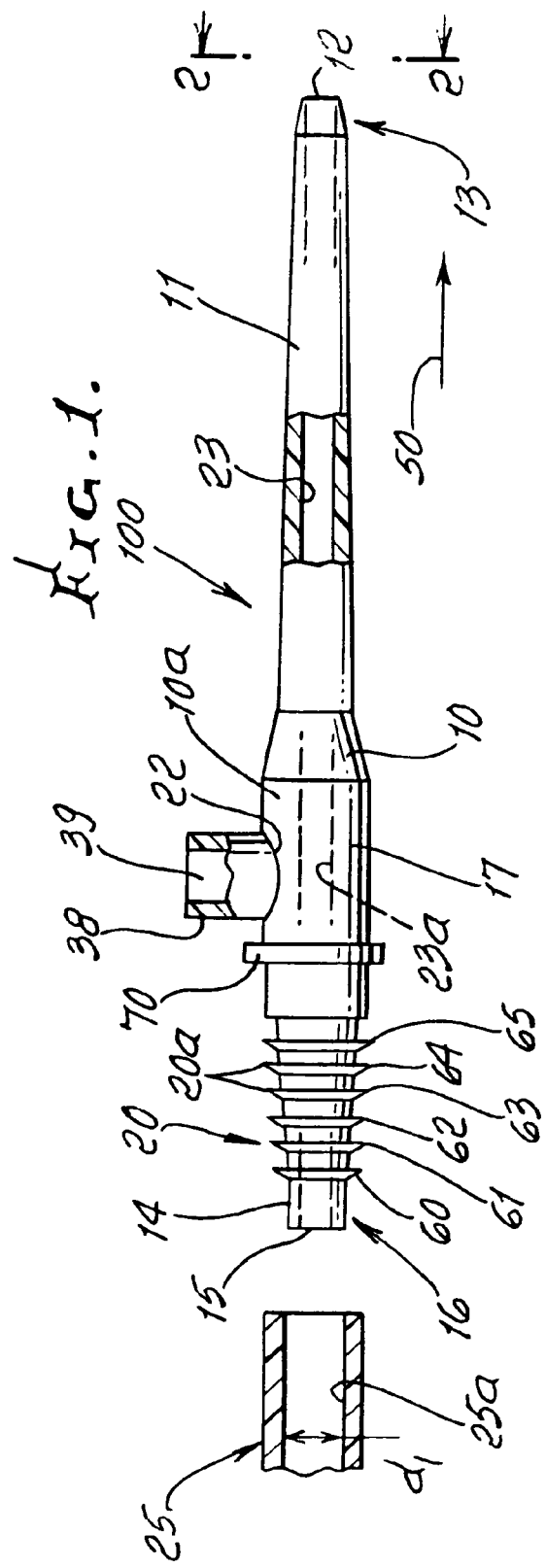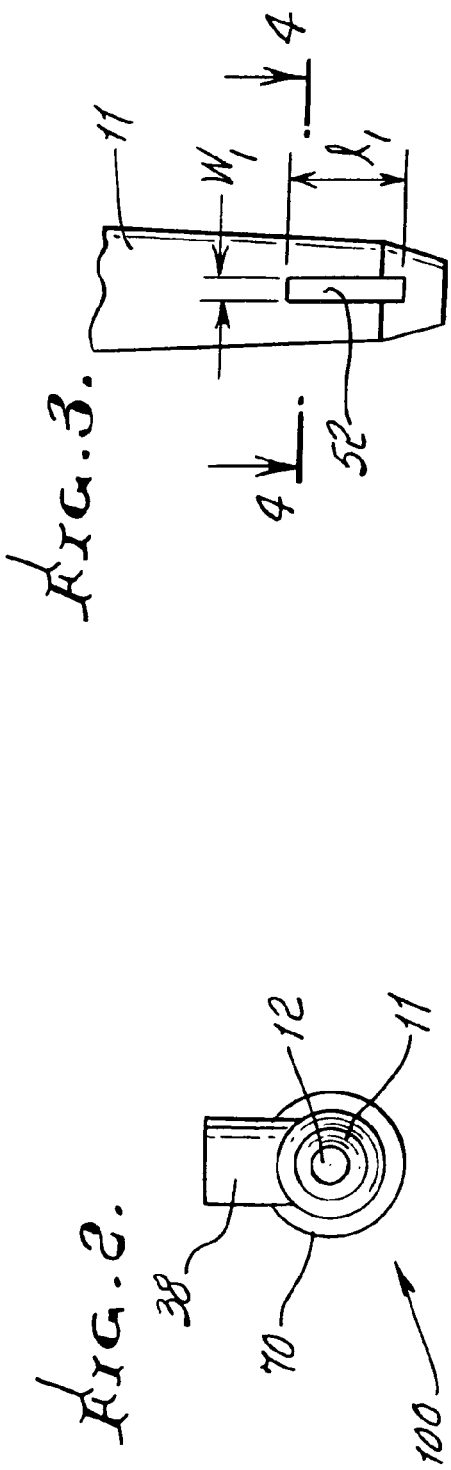

ANTIMICROBIAL FLUID SUCTIONING DEVICE

This application is a continuation-in-part of Ser. No. 12/217,593, filed Jul. 8, 2008 now U.S. Pat. No. 8,029,497.

BACKGROUND OF THE INVENTION

This invention relates generally to medical suctioning or aspiration devices and methods, and more particularly to an improved device and method characterized by increased overall utility, as well as ease and effectiveness of use and operation.

There is need for improvements in devices of the type referred to above. Also, there is need for devices and methods embodying the novel and unusual features of construction, modes of operation and results found in the device and methods of use embodied in the present invention. This invention improves upon the devices of U.S. Pat. Nos. 6,958,050 and 4,729,765, incorporated herein by reference.

SUMMARY OF THE INVENTION

It is a major object of the invention to provide an improved suctioning device and method of its use, as referred to. Basically, the device comprises:

a) a longitudinally elongated, generally tubular, one-piece plastic body, b) the body having an axially elongated tapered, first portion extending toward an inlet proximate one end of the body, c) the body having an axially elongated second portion extending toward an outlet proximate an opposite end of the body, d) radially outwardly extending annular retention rings on said body second portion, said rings having sharp annular peripheries and the rings being axially resiliently flexible and axially spaced apart, e) and there being body side porting between said body first and second portions, the side porting being manually controllable to control suction exertion, f) the body having outwardly presented antimicrobial surface extent.

Another object is to provide a body bore that has constant, i.e. unstepped, diameter between the inlet and outlet, and to provide the rings to have axially flexible molded plastic peripheries for establishing annular seals in response to axial reception of a connector tubing bore onto and over the body second portion. In this regard, the connector tubing that fits over the rings has a bore with interference engagement with at least three of said rings, whereby those three rings are flexed axially at their peripheries, thereby to establish annular seals. The rings are typically axially spaced apart on a body conical surface whereby each ring is independently axially flexible, the rings closer to the body first portion being flexed to greater extent than other rings, to establish greater local retention to the connector tubing. Accordingly, the degree of such retention can be more accurately controlled by and in response to the degree of push-on advancement of that tubing relative to the rings. The antimicrobial surface extent of the body, at and between the rings, serves antimicrobial functioning as respects bacteria that could collect in spaces between the rings, from tubing surfaces extending over the rings.

A further object is to provide the rings to have front and back flanks, and wherein for each pair of rings, the successive back flank of one ring of the pair is everywhere spaced axially from the front flank of the other ring of the pair whereby each ring is independently axially flexible. Typically, the back flanks extend at angles $\alpha$ relative to the axially elongated direction and the front flanks extend at angles $\beta$ relative to the axially elongated direction, and wherein $\beta > \alpha$ and $\alpha > 45°$, and said body second portion has a conical surface from which the rings project outwardly.

Yet another object is to provide a body side wall inlet to have elongated length $l_1$ in the length direction of the tubing elongated first portion, and has narrowed width $w_1$ along said length $l_1$, and wherein $l_1 \gg w_1$.

These and other objects and advantages of the invention, as well as the details of an illustrative embodiment, will be more fully understood from the following specification and drawings, in which:

DRAWING DESCRIPTION

FIG. 1 is a side elevation view of a preferred device incorporating the invention;

FIG. 2 is an end view taken on lines 2-2 of FIG. 1;

FIG. 3 is a top plan view taken on a modified device stem, showing a side inlet;

DETAILED DESCRIPTION

Figure 4:
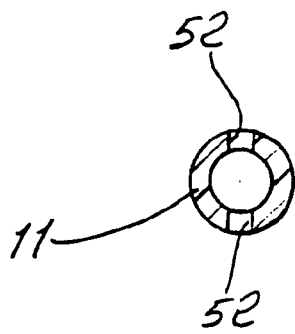
FIG. 4 is a section taken on lines 4-4 of FIG. 3.

The drawings show the improved and preferred multi-purpose medical suctioning device 100, which is of one-piece, integrally molded synthetic resinous (plastic) composition. It includes:

a) a longitudinally and axially elongated, generally tubular, one-piece plastic body 10, b) the body 10 having an axially elongated, tapered, first portion 11 extending toward an inlet 12 proximate an end 13 of the body, to receive fluid being suctioned, c) the body 10 having an axially elongated second portion 14, extending from an outlet 15 proximate an opposite end 16 of the body, and toward a body mid-portion 17, d) radially outwardly extending annular retention and sealing rings 20 on the body second portion 14, the thin rings having narrow and sharp annular peripheries 20a, and being axially stiffly resilient, and axially spaced apart, e) and the body having side porting 22 at the mid porting 17, and being manually or finger controllable to control suction exertion.

It will be seen that the body preferably has a continuous bore 23 extending between the body opposite ends 13 and 16, the bore having constant or substantially constant, unstepped diameter along the entire body length between such steps, whereby flow of suctional fluid is unimpeded, through the body and to connector tubing. Such tubing is shown at 25 in FIG. 1 before its push-on connection over rings 20, and also in FIG. 5 after such push-on connection.

Figure 5:
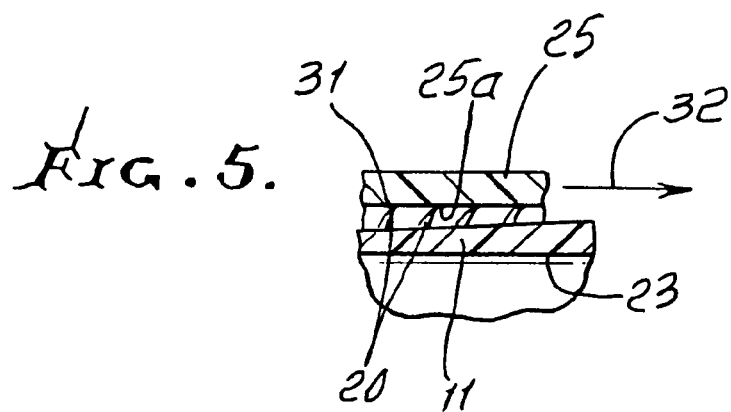
FIG. 5 is an enlarged fragmentary section, showing retention rings in the body and having peripheries engaging and being progressively and controllably flexed by engagement with the bore and connector tubing.

It will be noted that the rings are resiliently axially flexible, particularly at their peripheries 31, for establishing annular seals in response to axial reception, i.e. push-on, of the bore 25a of tubing 25 over the rings. The ring peripheries progressively increase in diameter, in the push-on direction 32, whereby the progressively forwardmost rings flex to greater progressive extent, for gripping the tubing bore, as seen in FIG. 5. Accordingly, the degree of gripping can be accurately controlled by the extent of push-on of the tubing, whereas, all or substantially all of the rings sub-tended by the connector tubing engage its bore to establish sealing at multiple locations, safe and full suctioning thereby being assured. The structure also accommodates tubing bore diameters that vary.

Figure 6:
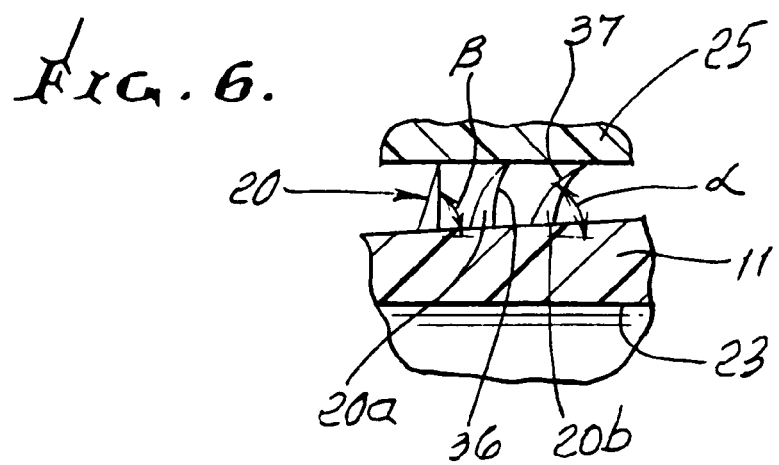
FIG. 6 is a still further enlarged section showing the angular relationships between ring front and rear flanks.

Note also in FIG. 6 that the rings have front flanks 36, and back flanks 37. For each pair of successive rings, as for example at 20a and 20b, the back flank 37 of ring 20b is everywhere spaced axially from the front flank 36 of ring 20a, whereby each ring is independently axially flexible, maintaining or enhancing the integrity of the sealing and anchoring (gripping) function, the back flanks extend at angles α relative to the axially elongated direction and the front flanks extend at angles β relative to the axially elongated direction, and wherein β>α, and α>45°, and said second portion 14 has a conical surface from which said rings project outwardly, the relatively forward ring flexed to greater extent than the next relatively rearward ring, the rings having outward projections greater than their axial thickness, the rings spaced along said conical surface having peripheries progressively increasing in diameter whereby the rings sequentially have increasingly flexed positions, and including connector tubing having a bore received onto and over said body second portion, said bore having interference engagement with at least three of said rings, whereby said three rings are flexed axially at said peripheries thereof to establish annular seals, The body 10 mid-portion has an integrally molded sidewise or transversely extending protrusion 38 defining a finger controllable air inlet 39 in communication with the side port 22. The body wall at 10a has substantially increased thickness outwardly from bore extent 23a at the body mid portion. This establishes a non flexible anchor region for manual gripping, which the body first portion 11 remain sidewise flexible to accommodate to the geometry of the anatomy, such as the mouth, being suctioned.

It will be noted that in FIGS. 1 and 2 the inlet 12 faces axially endwise, in the direction indicated by arrow 50.

In the FIGS. 3 and 4 modification, the inlet or inlets 52 face sidewise, i.e. transversely relative to the longitudinally axial extent of the body first portion 11 shown. Each such inlet preferably has elongated length $l_1$ in the longitudinal direction of 11, and has narrowed width $w_1$ along the length $l_1$ wherein $l_1 \gg w_1$. The slot configuration of the inlet to the bore, enhances inlet fluid flow access, directionally, to the bore, and suction access to the in-flow, along the bore.

Preferred highly advantageous operative dimension of the rings are as follows:

| Ring | overall diameters (inches) | ring thickness inches | spacing between rings |
|---|---|---|---|
| 60 | ≈.324 | .031 | .069 |
| 61 | ≈.335 | " | " |
| 62 | ≈.350 | " | " |
| 63 | ≈.360 | " | " |
| 64 | ≈.375 | " | " |
| 65 | ≈.375 | " | " |

The annulus 70 on the body acts as a firm step to limit push-on of the connector tubing, at the body mid-portion.

It will be understood that the plastic body 10 has outwardly present antimicrobial surface extent, as for example the entire surface of the body. Such antimicrobial surface extent includes body surfaces located at and between the rings, and over which tubing 25 is assembled to close off spaces between the rings. The antibacterial surfaces act to prevent growth of commonly occurring organisms such as *E. coli, staph*, and *candida* which could be dispersed from the bore 25a of the assembled tubing into spaces between the rings and onto the rings.

Figure 6A:
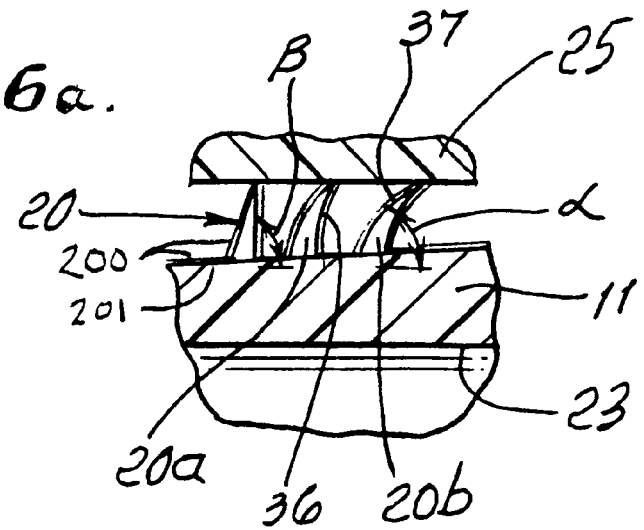
FIG. 6a is a view like FIG. 6, but showing antimicrobial use.

The antimicrobial surface extent may be presented by the body itself, as by ionic bonding of antibiotic(s) to the plastic or polymer substance of the body; as by blending into the body plasic or by coating of antibiotics to the body surface, or by use of silver or silver salt(s) bonded to the body (substrate) surface. FIG. 6a shows such a coating 200 on a body surface 201, and also on rings 20, exposed to assembled tubing.

Figure 7:
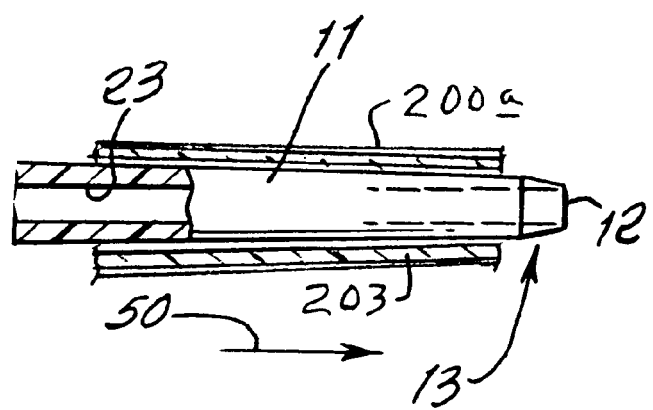
FIG. 7 shows antimicrobial substance on a sleeve or cover received endwise over the device.

FIG. 7 shows such a coating 200a on a protective tubular plastic sheath or cover 203, removably covering the body and rings or by antibiotic blending into such plastic. The sheath may typically cover the entire body, and the antimicrobial substance may coat the entire sheath, or be bonded to the sheath material, so as to be exposed at its surfaces, internal and external. The sheath is removed when tubing 25 is to be endwise assembled to the body, for suction use or application as at 38 and 39 in FIG. 1.

The body itself may consist of a polymer such as PVC, or other polymers.

We claim:

1. A mucous suction device, comprising in combination:
    a) a longitudinally elongated, generally tubular, one-piece plastic body,
    b) said body having an axially elongated tapered first portion extending toward an inlet proximate one end of the body,
    c) said body having an axially elongated second portion extending toward an outlet proximate an opposite end of the body,
    d) radially outwardly extending annular retention rings on and integral with said body second portion, said rings having sharp annular peripheries and said rings being axially resiliently flexible and axially spaced apart, each ring having in an axially elongated direction a front flank and a back flank, and wherein for each pair of successive rings, the back flank of a relatively forward ring is everywhere spaced axially forwardly from the front flank of the next relatively rearward ring, whereby each ring is independently axially flexible, maintaining or enhancing the integrity of the sealing and anchoring function, the back flanks extend at angles α relative to the axially elongated direction and the front flanks extend at angles β relative to the axially elongated direction, and wherein β>α, and α>45°, and said second portion has a conical surface from which said rings project outwardly, the relatively forward ring flexed to greater extent than said next relatively rearward ring, each ring having outward projection substantially greater than the ring axial thickness everywhere between said conical surface and ring tips, the rings spaced apart along said conical surface and having peripheries progressively increasing in diameter at successive rings locations in said direction, whereby the rings sequentially have increasingly flexed positions, there being gaps formed between oppositely facing flanks of successive rings, said gaps extending outwardly adjacent said flanks and from said conical surface, the gaps having radially outward dimensions to the ring tips substantially greater than gap width nearest said conical surface of said body second portion, and including connector tubing having a bore received onto and over said body second portion, said bore having interference engagement with at least three of said rings, whereby said three rings are flexed axially at said peripheries thereof to establish annular seals, e) and there being body side porting between said body first and second portions, said side porting being manually controllable to control suction exertion, f) there being antimicrobial substance associated with body outwardly presented plastic surface extent at said first and second portions, said substance extending at and on and coating said rings and said ring sharp peripheries, to flex therewith, said substance extending in said gaps and coating said conical surface between successive rings.

2. The device of claim 1 wherein the body has a bore extending between said inlet and outlet, said bore having substantially constant diameter along entire body length.

3. The device of claim 1 wherein said body portion and said rings consist of molded plastic material.

4. The device of claim 3 wherein said body portions are translucent.

5. The device of claim 1 wherein said inlet faces axially endwise.

6. The device of claim 1 wherein said inlet faces sidewise relative to said body elongated second portion.

7. The device of claim 6 wherein said inlet has elongated length $l_1$ in the length direction of said body elongated first portion, and has narrowed width $w_1$ along said length $l_1$, and wherein $l_1 \gg w_1$.

8. The device of claim 1 wherein the body has a midportion between said first and second portions, said side porting located at said body mid-portion, there being a sideward protrusion integral with said mid-portion, said protrusion defining a finger controllable air inlet in communication with said side porting.

9. A suctioning device comprising in combination:

a) an elongated, generally tubular, plastic body, b) said body having an axially elongated tapered first portion extending toward an inlet proximate one end of the body, c) said body having an axially elongated second portion extending toward an outlet proximate an opposite end of the body, d) radially outwardly extending annular retention rings on said body second portion, said rings having sharp annular peripheries and said rings being axially resiliently flexible and axially spaced apart, e) and there being body side porting between said body first and second portions, said side porting being manually controllable to control suction exertion, f) said rings being axially flexible at said peripheries for establishing annular seals in response to axial reception of a connector tubing bore onto and over said body second portion, g) said body having outwardly presented antimicrobial surface extent, at and on all of the rings and their sharp peripheries, to flex therewith, the rings having outward projections substantially greater than ring axial thickness, h) each ring having in an axially elongated direction a front flank and a back flank, and wherein for each pair of successive rings, the back flank of a relatively forward ring is everywhere spaced axially forwardly from the front flank of the next relatively rearward ring, whereby each ring is independently axially flexible, maintaining or enhancing the integrity of the sealing or anchoring function, the back flanks extending at angles $\alpha$ relative to the axially elongated direction and the front flanks extending at angles $\beta$ relative to the axially elongated direction, and wherein $\beta > \alpha$, and $\alpha > 45°$, and said second portion has a conical surface from which said rings project outwardly the relatively forward ring flexed to greater extent than said next relatively rearward ring, each ring having outward projection substantially greater than the ring axial thickness everywhere between said conical surface and ring tips, the rings spaced along said conical surface having peripheries progressively increasing in diameter at successive ring locations in said direction, whereby the rings sequentially have increasingly flexed positions, there being gaps formed between oppositely facing flanks of successive rings, said gaps extending outwardly adjacent said flanks and from said conical surface, the gaps having radially outward dimensions to the ring tips substantially greater then gap widths nearest said conical surface of said body second portion, and including connector tubing having a bore received onto and over said body second portion, said bore having interference engagement with at least three of said ring, whereby said three rings are flexed axially at said peripheries thereof to establish annular seals, i) there being antimicrobial substances extending in said gaps and coating said conical surface between successive rings.

10. The device of claim 9 including a connector tubing having a bore received onto and over said body second portion, said bore having interference engagement with at least three of said rings, whereby said three rings are flexed axially at said peripheries thereof to establish annular seals.

11. The device of claim 9 wherein said inlet faces axially endwise.

12. The combination of claim 9 wherein said inlet faces sidewise relative to said body elongated second portion.

13. The device of claim 12 wherein said inlet has elongated length $l_1$ in the length direction of said body elongated first portion, and has narrowed with $w_1$ along said length $l_1$, and wherein $l_1 \gg w_1$.

14. The device of claim 9 wherein the body has a bore extending between said inlet and outlet, said bore having substantially constant diameter along entire body length.

15. The device of claim 14 wherein said antimicrobial surface extent includes body surfaces located at and between said rings.

16. The device of claim 9, wherein said antimicrobial surface extent includes at least one of the following:
   i) silver
   ii) silver salt
   iii) antibiotic substance.

17. The device of claim 16 including cover in the form of a sleeve fitting endwise on said device, said sleeve also having antimicrobial surface extent.

* * * * *